US00PP16356P3

(12) United States Plant Patent
van Dijk

(10) Patent No.: US PP16,356 P3
(45) Date of Patent: Mar. 21, 2006

(54) *ANTHURIUM ANDREANUM* PLANT NAMED 'ANTHBONDEM'

(50) Latin Name: *Anthurium andreanum*
Varietal Denomination: Anthbondem

(75) Inventor: Jan van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 217 days.

(21) Appl. No.: 10/612,052

(22) Filed: Jul. 3, 2003

(65) Prior Publication Data

US 2005/0005336 P1 Jan. 6, 2005

(51) Int. Cl.
*A01H 5/00* (2006.01)

(52) U.S. Cl. ..... Plt./365
(58) Field of Classification Search ..... Plt./365
See application file for complete search history.

*Primary Examiner*—Anne Marie Grunberg
*Assistant Examiner*—Annette H Para
(74) *Attorney, Agent, or Firm*—Foley & Lardner, LLP

(57) ABSTRACT

A new and distinct cultivar of *Anthurium andreanum* plant named 'Anthbondem', as described and illustrated, and particular characterized by the combined features of Compact plant growth and early and rich flowering; mini-type pot plant; maximum growth to approximately 30 cm; long and erect peduncle; flowers held above the foliage; full plant habit due to very rich shoot formation; dark green leaves, very compact, durable with light green primary veins; red and reasonably durable flowers, flowers remain red until they die; large amount of flowers in relation to the amount of leaves, resulting in an excellent leaf to flower size ratio.

4 Drawing Sheets

Latin name of the genus and species of the plant claimed: *Anthurium andreanum* L.
Variety denomination: Anthbondem.

BACKGROUND OF THE INVENTION

'Anthbondem' is a new and distinct cultivar of *Anthurium,* botanically known as *Anthurium andreanum* L. The new cultivar is a product of a planned breeding program, and was obtained from a cross made during such a program in Bleiswijk, The Netherlands, in 1997.

The female or seed parent was a pink-colored *Anthurium* pot plant identified as number 95-634-01 (unpatented). The male or pollen parent was an orange-colored flowering *Anthurium* pot plant identified as number 94-00-175 (proprietary, unpatented). 'Anthbondem' was discovered and selected as a flowering plant within the progeny of the stated cross by the inventor, Jan van Dijk, in April, 1999 in a controlled environment in a glasshouse in Bleiswijk, The Netherlands.

Subsequent asexual reproduction by tissue culture in agar in Bleiswijk, The Netherlands, has demonstrated that the combination of characteristics as herein disclosed for the new cultivar are firmly fixed and are retained through successive generations of asexual reproduction.

BRIEF DESCRIPTION OF THE INVENTION

The following traits have been repeatedly observed and in combination distinguish 'Anthbondem' as a new and distinct cultivar:

1. Compact plant growth and early and rich flowering;
2. Mini-type pot plant; maximum growth to approximately 30 cm;
3. Long and erect peduncle; flowers held above the foliage;
4. Full plant habit due to very rich shoot formation;

5. Dark green leaves, very compact, durable with light green primary veins;
6. Red and reasonably durable flowers, flowers remain red until they die;
7. Large amount of flowers in relation to the amount of leaves, resulting in an excellent leaf to flower size ratio.

Of the many cultivars known to the present inventor, the most similar in comparison to 'Anthbondem' is the *Anthurium andreanum* cultivar 'Antnerom' (as disclosed in U.S. Plant Pat. No. 13,414). Plants of 'Anthbondem' differ from plants of 'Antnerom' primarily in shoot formation and flower shape. 'Anthbondem' has very rich shoot formation whereas 'Antnerom' has moderate shoot formation. The flowers of 'Anthbondem' are round in shape whereas the flowers of 'Antnerom' are ligulate in shape.

BRIEF DESCRIPTION OF THE DRAWINGS

The accompanying photographs, taken in Bleiswijk, The Netherlands, show typical 'Anthbondem' specimens.

FIG. 1 is a side-view of 'Anthbondem' showing the flowers just above the leaf canopy.

FIG. 2 is a close-up of an 'Anthbondem' flower showing the spathe and spadix.

FIG. 3 is a close-up of 'Anthbondem' flowers at three different stages of development: from young on the left to old on the right. The youngest flower has an unripe spadix (pistils and pollen are not visible yet). The flower in the middle has a ripe spadix. The spathe of the old flower on the right becomes dark-red. There is a difference in age of approximately 8 to 10 weeks between the flower depicted on the left and the flower depicted on the right.

FIG. 4 is a close-up of the top of a young (left) and an old leaf blade (right) showing the difference between young and old leaf blades. It also shows that the young leaf blades are more shiny then the old leaf blades.

DETAILED BOTANICAL DESCRIPTION

The following observations, measurements and values describe an 'Anthbondem' plant which was 66 weeks old, from the date that the plants were planted from tissue culture into plugs, in a greenhouse in Bleiswijk, The Netherlands, under greenhouse conditions which closely approximate those generally used in horticultural practice.

Color references are made to The Royal Horticultural Society (R.H.S) Colour Chart, except where general color terms of ordinary significance are used. The color references are approximate, as color depends to a degree on horticultural practices such as light level and degree of fertilization, among others. The color values were determined between 11:00 a.m. and 3:00 p.m. on Mar. 25, 2003, under 5000 lux natural light in a glasshouse in Bleiswijk, The Netherlands. The phenotype may vary significantly when grown under different conditions of temperature, light or other determining factors, without a change in genotype of the plant.

PROPAGATION

Asexual propagation by means of tissue culture and all subsequent propagation that flowered have been true to the original type in plant and flower characteristics.

PLANT DESCRIPTION

Approximately 55–60 weeks following division, 'Anthbondem' will reach a mature size of approximately 20 cm to 25 cm in height and approximately 25 cm to 30 cm in width in a 14 cm container. However, 'Anthbondem' can be easily grown to a smaller size for example, 20 cm in height, when it is placed in a 12 cm container.

LEAVES

Form: The leaf blade is elliptical-cordate with an acuminate tip and a cordate base. The leaf blade angle with the petiole between 90 and 120 degrees. 'Anthbondem' makes slightly larger leaf blades as it ages. 'Anthbondem' also produces a lot of axillary shoots with small leaf blades. Therefore, a wide range in leaf blade length and width is found on each plant. The minimum leaf blade length is approximately 3 cm and the maximum leaf blade length is approximately 10 cm. The minimum leaf blade width is approximately 1.5 cm and the maximum leaf blade length is approximately 8 cm.

Texture: The leaf blades are shiny, leathery and thick. The mature leaf blades are weakly cupped. The young leaf blades are more shiny then the old leaf blades.

Veins: The mid-vein and primary veins (the veins which radiate out from the juncture of the petiole and leaf) protrude at the underside of the leaf blade. In young leaves (younger than 4 weeks) the color of the veins is brown-red (RHS 178A). In older leaf blades (approximately more then 4 weeks) the green color of the veins at the upper surface (RHS 146A) and the lower surface (RHS 147C) of the mid-vein and primary veins (approximately 4 to 6) contrast with the darker green color of the surface of the leaf blade.

Leaf blade-color: Of a young leaf blade (approximately maximum 4 weeks old) the upper surface is colored dark green (RHS 147A). On an old leaf blade (approximately more than 4 weeks) the upper surface is green (RHS 139A) and the lower surface is green (RHS 146B).

Lobes: A leaf blade has two small lobes extending past the petiole. The distance between the petiole and leaf juncture to the highest point on the lobes of mature leaf blades (width 7 cm, length 10 cm) ranges approximately from 1.5 to 2.5 cm.

Petiole: The color of the petiole of an old leaf blade is brown-green (RHS 148A). The color of the petiole of a young leaf blade is brown-red (RHS 183A). The cross section of the petiole is round and the diameter is approximately 2 to 3 mm. The color of the cataphyls surrounding the petioles is brown-red (RHS 178B).

SPATHE

Buds: The spathe is tightly rolled around the spadix and extrudes from the peduncle sheath. After the spathe is fully open, the peduncle elongates a few centimeters.

Size: The completely developed spathe of a 25 cm tall plant is approximately 5 cm to 6 cm long and approximately 6 cm wide.

Color: When the spathe is just fully open the upper surface is red (RHS 45B) and the lower surface is pink-red (RHS 51A). Approximately 7 to 8 weeks after opening, the spathe discolors to dark-red (RHS 153A). After approximately another 12 to 16 weeks the complete flower will die off.

Arrangement: The spathe angle with the peduncle is between 110 and 130 degrees. The spathe stand on a straight wiry peduncle approximately 3 cm to 5 cm above the foliage. The peduncle cross-section is round and the diameter approximately 2 mm to 3 mm, depending on the age of the plant. The peduncle is erect, the length ranging from approximately 13 to 20 cm.

Shape: The spathe is ovate with a mucronate tip and an open cordate base. A just fully opened spathe is slightly cup-shaped. The lobes of the spathe tend to move downwards when the flower ages.

FLOWERING TIME

One small untreated tissue culture plant of approximately 2 cm tall will flower, depending on season, after approximately 15 to 16 months when approximately 2 to 3 blossoms will appear. More blossoms appear some week so that a full flowering and salable plant can have 4 to 10 red flowers. Smaller blossoms may occur on less mature growth.

REPRODUCTIVE ORGANS

Size: The spadix measures approximately 2 to 3 cm in height. The length of the spadix is equal to the length of the spathe. The spadix is a little columnar. When the spadix is mature (approximately 3 cm long) it is approximately 5 mm to 6 mm at the base and 4 mm to 5 mm at the top. The spadix angle with spathe is approximately 50 to 70 degrees. The angle increases when the flower matures.

Color: When the spathe unrolls the spadix is unripe. Later as the spadix matures, pistils become visible and some pollen might occur. An unripe spadix is orange-red (RHS 172C) at the base and brown-red (RHS 172B) at the top. As the spadix ripens, it turns from orange-brown (RHS 172B) to orange-red (RHS 35A) to pink (RHS 154C). Berries exist on the spadix when pistils have been pollinated, and the spadix will become green.

Stamens: Anthers and filaments are not clearly visible on the spadix.

Pollen: Little production, white in color.

Pistil: An unripe pistil is orange-red (RHS 172C) at the base and brown-red (RHS 172B) at the top. As the pistil ripens, it turns from orange-brown (RHS 172B) to orange-red (RHS 35A) to pink (RHS 154C). The pistil protrudes from the spadix.

Seeds:

*Quantity.*—1 seed per berry (fruit).

*Shape.*—Round to oblong, slightly flattened off on two sides.

*Length.*—About 0.3 cm.

*Diameter.*—About 0.2 mm.

*Texture.*—Smooth and slimy.

*Color.*—Greyed-orange, RHS 163C. Seed color may differ (lighter or darker) throughout the season and depends on the ripening stadium of the berry.

Fruit:

*Quantity.*—Number varies after pollination; ranges from 1 to 140 berries.

*Size.*—Grows from 0.1 cm just after pollination to 0.4 cm after about 26 weeks.

*Color.*—Unripe: Green, RHS 137B. Ripe: Grey-orange, RHS 169B to 169C.

ROOTS

Pinkish-white roots with smaller hairy laterals. The root-tips are yellow.

DISEASE/PEST RESISTANCE

No known resistance and/or susceptibility to diseases and pests.

I claim:

1. A new and distinct *Anthurium andreanum* plant named 'Anthbondem', as herein described and illustrated.

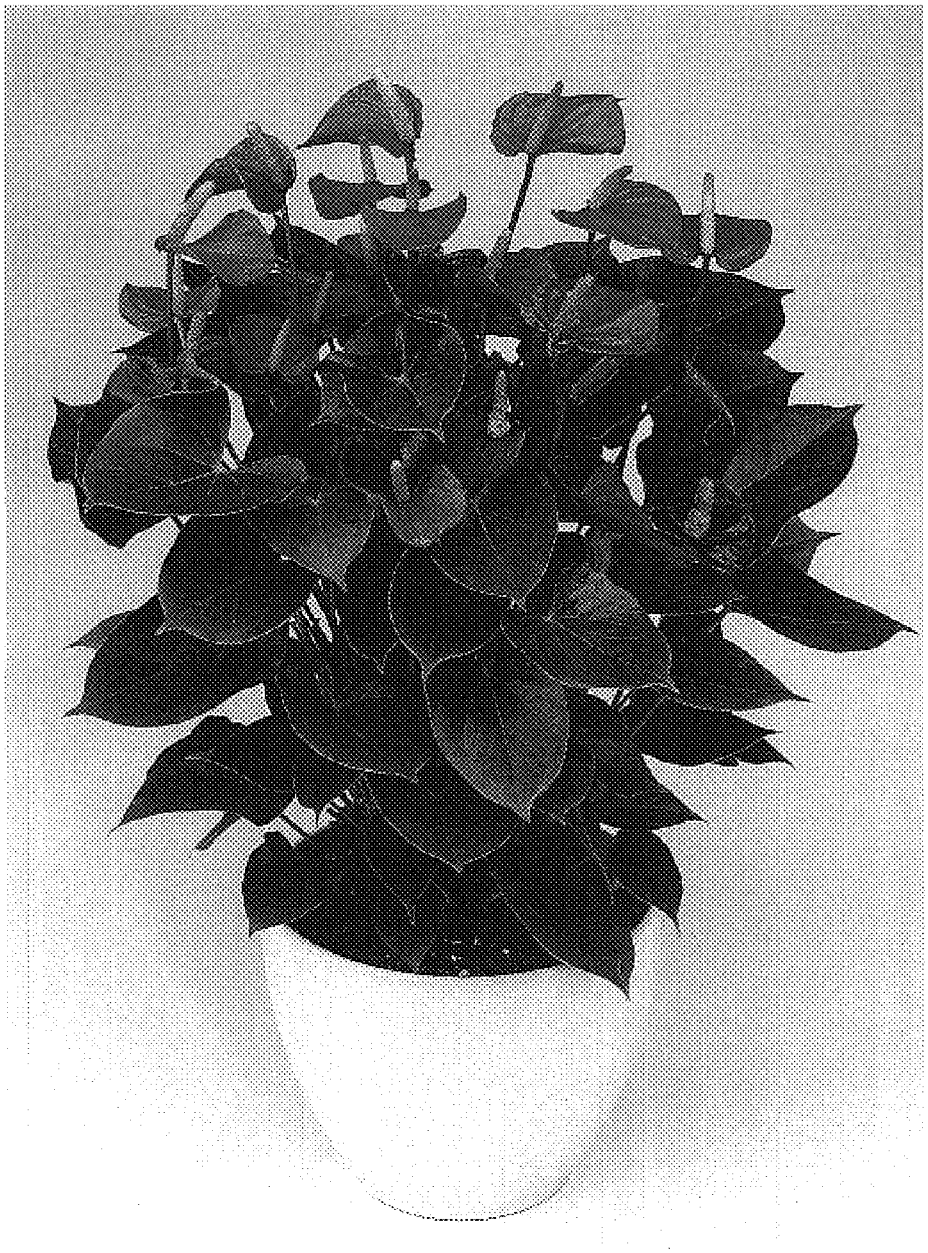

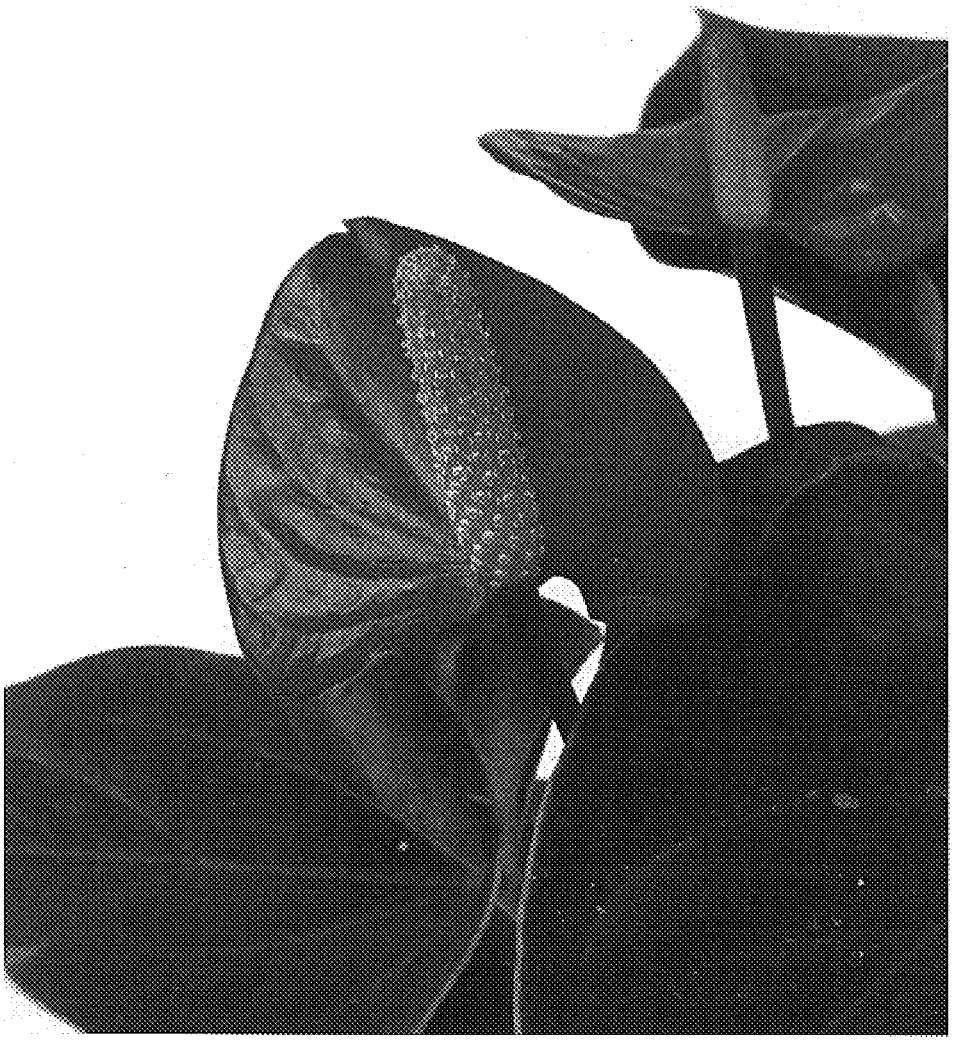

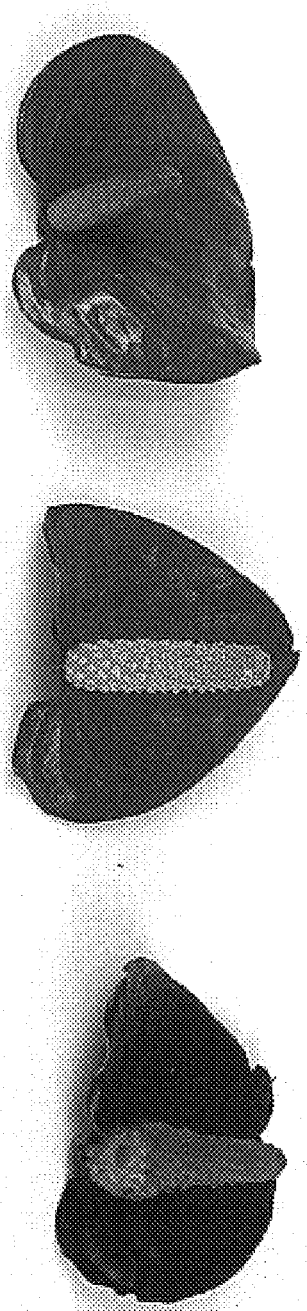

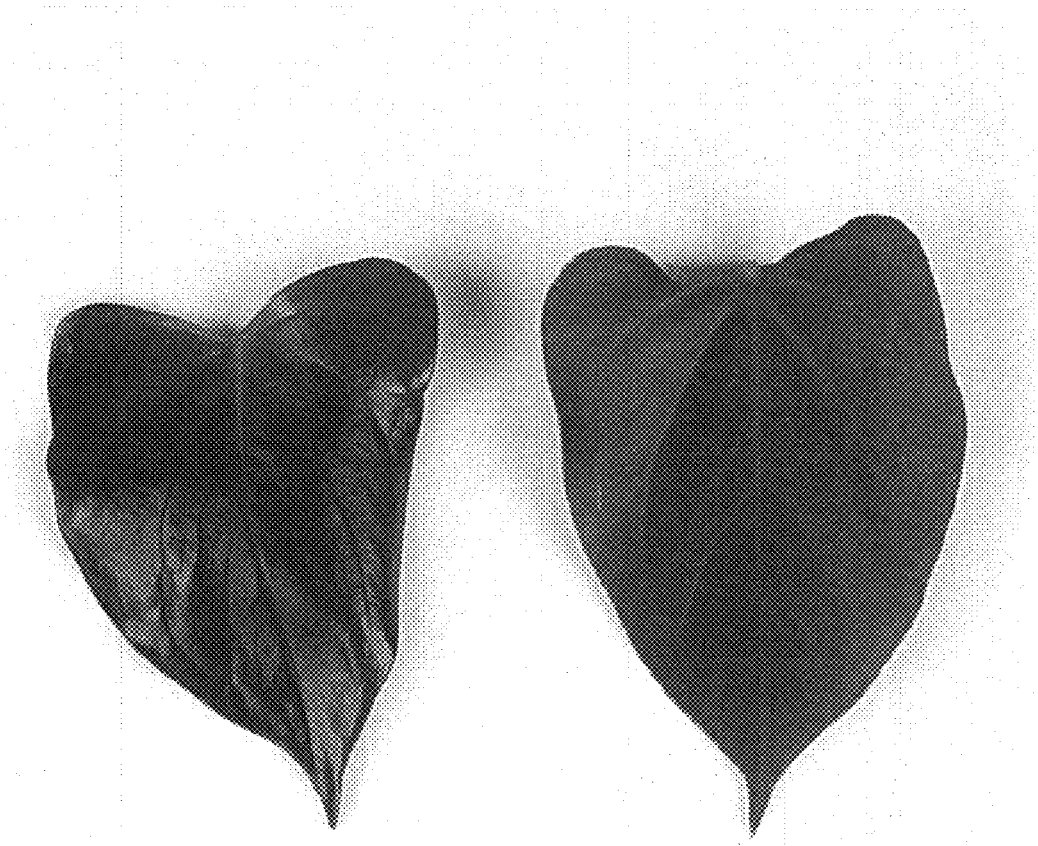

* * * * *